Figure 1:
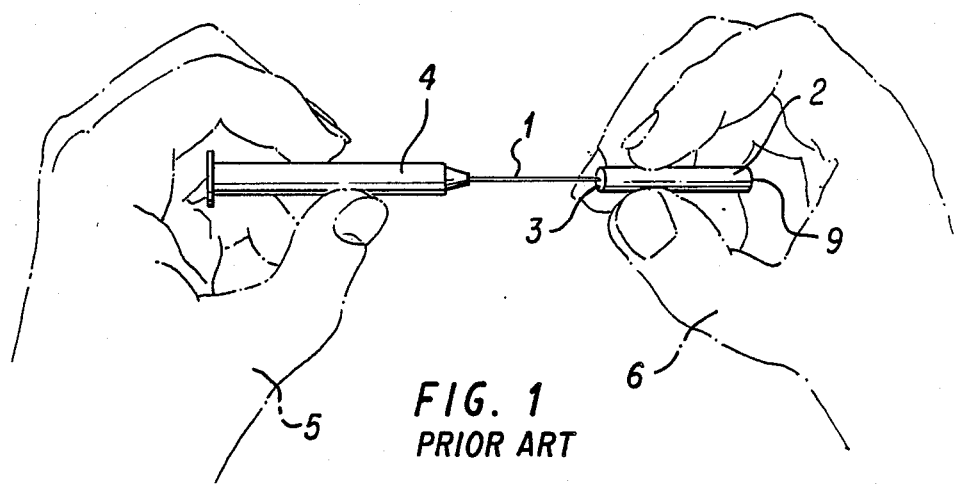

United States Patent [19]
Roberts

[11] Patent Number: 4,906,235
[45] Date of Patent: Mar. 6, 1990

[54] NEEDLE GUARD

[76] Inventor: Christopher W. Roberts, P.O. Box 445, Derby Line, Vt. 05830

[21] Appl. No.: 258,789
[22] Filed: Oct. 17, 1988

Related U.S. Application Data

[63] Continuation-in-part of Ser. No. 234,559, Aug. 22, 1988.

[51] Int. Cl.⁴ ............................................. A61M 5/32
[52] U.S. Cl. .................................... 604/192; 604/263
[58] Field of Search ....................... 604/187, 192, 263

[56] References Cited

U.S. PATENT DOCUMENTS

| | | | |
|---|---|---|---|
| 4,559,042 | 12/1985 | Votel | 604/192 |
| 4,629,453 | 12/1986 | Cooper | 604/192 |
| 4,735,617 | 4/1988 | Nelson et al. | 604/192 |
| 4,740,204 | 4/1988 | Masters et al. | 604/192 |

*Primary Examiner*—John D. Yasko
*Attorney, Agent, or Firm*—Edward McC. Roberts

[57] ABSTRACT

A needle guard for use with a hypodermic syringe comprising a substantially cylindrical hollow body, having a first end that is open and a second end that is closed, wherein said guard has attached to an external surface thereof and projecting therefrom a grasping tab adapted so that the user can hold the body of the needle guard by grasping the tab, thus removing the user's hand from the projected line of force described by the insertion of the needle into the needle guard. The improved needle guard reduces the incidence of accidental puncture wounds which users of hypodermic syringes often experience.

2 Claims, 2 Drawing Sheets

NEEDLE GUARD

This application is a continuation-in-part of copending application Ser. No. 234,559, filed Aug. 22, 1988.

This invention relates to a needle guard for use with a hypodermic syringe, and more specifically to a needle guard having means adapted to lessen the likelihood that the user will accidentally suffer a puncture wound when inserting the needle into the guard as for storage or disposal after use.

Modern medical techniques have resulted in the extensive use of hypodermic needles to obtain blood samples, to give injections and for infusions. One of the problems which has occurred as a result of frequent use of the existing products has been undesired puncture wounds suffered by persons employing hypodermic needles, such as physicians, nurses and laboratory workers as well as technicians, orderlies and housekeepers. Such inadvertent puncture wounds have necessitated treatment of injury and frequently treatment of diseases that result from the wounds. Such injuries and illnesses are troublesome not only in a physical sense, but also financially as a result of the ultimate cost in terms of lost employee time, the cost of treating the injuries and the associated record-keeping. This is in addition to the pain, anguish and worry that may be experienced by the injured worker.

In general, existing systems provide a cap member having a closed end wall positioned over a needle which is attached to a syringe. The cap member serves as a guard for the needle to keep the needle from making undesired punctures when the needle is not in use. In use, the cap is removed and blood is drawn or an infusion is carried out. The needle may then be disposed of without recapping or, alternatively, the needle is then recapped by inserting the pointed end of the needle into the open end of the elongated cap member, that is the needle guard, and the needle is then disposed of.

A recent study has shown that approximately 30% of accidental puncture wounds which result from use of hypodermic needles have been due to accidents during recapping. Another 30% were found to have occurred as a result of exposed, used, but un-recapped needles being left in dangerous positions, such as on beds or in trash containers. See Hollenbaugh, *Hospital Employee Health*, April 1982, and McCormick et al., *American Journal of Medicine*, April 1981.

With respect to accidental needle sticks, with needles which have had patient contact, viral hepatitis is commonly a potential risk. Other diseases which may be transmitted in like fashion are herpes, streptococcus, staphylococcus, tuberculosis, malaria, syphilis and AIDS. In view of the potential seriousness of the diseases which may be contracted by post-patient contact through accidental needle sticks, hospitals and other health-care institutions have found it necessary to conduct extensive testing and treatment in order to minimize the risk of the accident victim's contracting a disease.

Various types of needle guards are known, such as those of U.S. Pat. Nos. 3,537,452, 3,865,236, 4,419,098, 4,438.845 and 4,643,722.

In spite of the foregoing, there remains a need for a cheap, effective, and easy-to-use needle guard for hypodermic syringes which will effectively cover the needle, maintain sterility and minimize the risk of accidental puncture wounds.

The above-described needs have been met by the instant invention which provides a needle guard with a grasping tab, use of which effectively removes the user's hand that holds the guard from the line of movement and force of the needle being inserted into the guard by the user's other hand. Consideration of the drawings will make clear different objects and aspects of the invention.

FIG. 1 is view of the commonly-used prior art needle guard in use. The view depicted is at the moment the needle is being inserted into the needle guard. With the syringe in one hand and the needle guard in the other, the hand holding the needle guard is necessarily directly in the line of forward movement of the thrusting needle.

Figure 2:
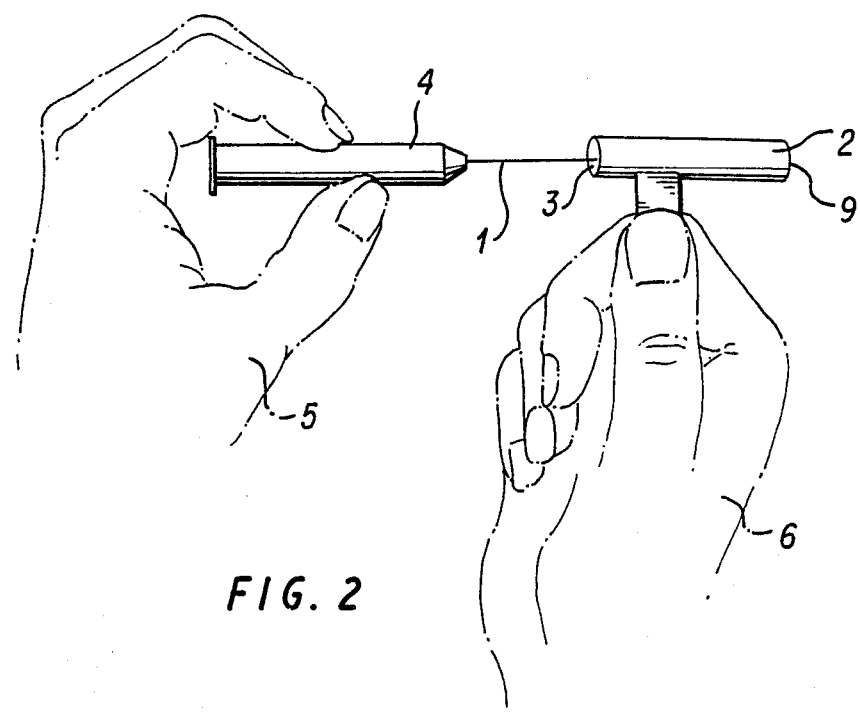
Figure 3:
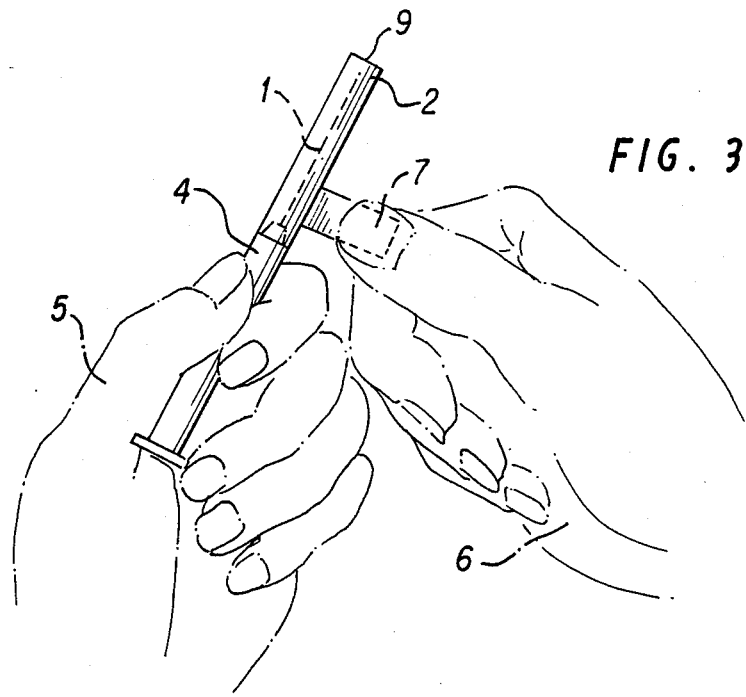

FIGS. 2 and 3 are views of the inventive needle guard in use. FIG. 2 depicts the moment the needle is being inserted into the needle guard, the same moment as depicted in FIG. 1 for the prior art. FIG. 3 depicts the moment the inserting thrust of the needle is complete and the covering of the needle by the guard is complete.

Figure 4:
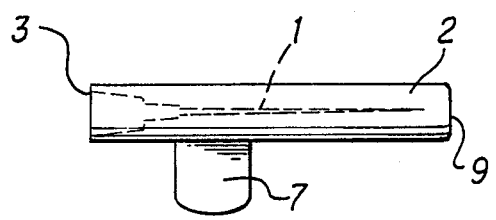
Figure 5:
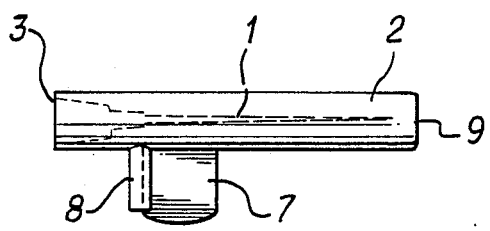
Figure 6:
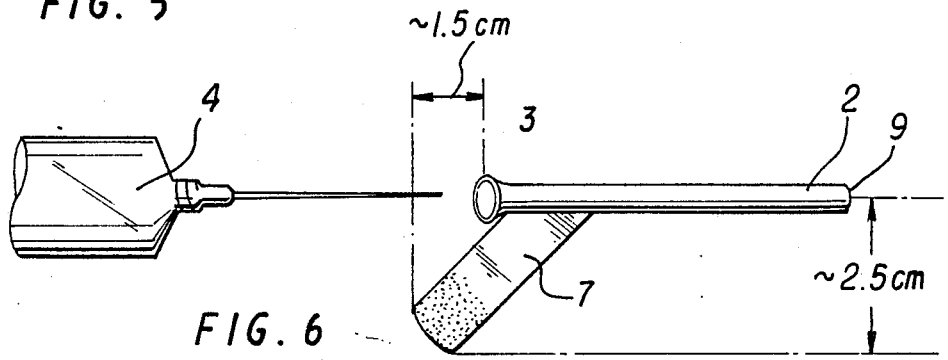

FIGS. 4–6 depict three species of the invention. FIG. 4 depicts the invention in its simplest aspect. FIG. 5 depicts a further modification, including an attached perpendicular shield. FIG. 6 depicts an improved diagonally-projecting grasping tab.

In each of the drawings, FIGS. 1–6, the numbered parts, insofar as they occur in each of the drawings, are the same in each drawing.

In each of FIGS. 1–3, a needle 1 is being inserted or is inserted into a cylindrical closure member 2, having a walled, closed end 9 and an open end 3, by means of which the needle's 1 insertion into the closure member 2 is effected. The needle 1 is attached, in use, to a syringe 4 which is held in one hand 5 while the closure member 2 is held in the other hand 6.

In FIGS. 2–6, in addition to all or some of the parts defined above, there is seen the inventive grasping tab 7 attached to the closure member 2. In FIGS. 2 and 3, it is seen that when the user grasps tab 7 in hand 6, said hand is effectively removed from the line of thrust of the needle 1 as it is being inserted into the closure member 2. In this manner, use of the instant invention, including a closure member 2 with an attached grasping tab 7, effectively reduces the likelihood of accidental needle punctures occasioned by the use of hypodermic syringes.

FIG. 5 is like FIG. 4 in that it shows the inventive closure member 2 with attached grasping tab 7, but it shows the further modification of having a generally sheet-like shield 8, bisected by the tab 7, normal to the plane of said tab 7 and attached to said closure member 2.

From the above description and Figures, it can be seen that the inventive needle guard comprises the cylindrical closure member 2 which is a substantially cylindrical hollow body, having a first end that is open and a second end that is closed. The needle guard is adapted to receive the needle of a hypodermic syringe by means of insertion into the first end of the guard. The inventive needle guard further has attached to an external surface thereof and projecting therefrom, closer to the first end than the second end thereof, a tab of a size and shape to be readily grasped between the thumb and forefinger of a user for insertion of the hypodermic needle into the first end of the needle guard without having the user's hand which holds the needle guard in the line of force of the inserting hand. Thus, use of the inventive needle guard will greatly reduce the likelihood of accidental stabbing of the user's hand. Particularly useful is the improved needle guard wherein the plane of the grasping tab is parallel to the length of the needle guard.

A particularly advantageous needle guard is one wherein the tab is molded of the same thermoplastic material as the body of the needle guard. Part of the advantage of this embodiment is the ease and economy of manufacture.

A further improvement of the inventive needle guard can be realized by texturing the surface of the grasping tab for easy and effective grasping. Particularly useful is a tab wherein the textured surface is formed of parallel ridges running transverse to the direction of movement of the user's thumb and forefinger. That is to say, useful texturing is formed by parallel ridges which run up an down the length of the tab.

As a further useful improvement of the inventive needle guard, it is particularly useful to have as a further attachment to an external surface of the needle guard a substantially, planar sheet-like shield, attached immediately next to the tab, between the tab and the first end of the body of the needle guard, the plane of the sheet-like shield being substantially bisected by the projecting edge of the tab and intersecting the body of the needle guard perpendicularly to the length of the body of the needle guard. As can be appreciated by the artisan, the sheet-like shield can be advantageously molded of the same thermal plastic material as the needle guard and the grasping tab, with all being formed in a single molding.

Although it is immaterial what material is used for manufacturing the improved needle guard, polyethylene, polypropylene, and the like have been found to be particularly useful materials in fashioning the improved needle guard.

A particularly preferred species of the invention is that of FIG. 6 where the grasping tab projects diagonally away from the cylindrical closure member of the needle guard so as to extend at least about 1.5 cm. beyond the open end of the needle guard and at least about 2.5 cm. from the axis of the needle guard. This diagonal projection from the needle guard body provides separation of the user's hand from the path of the needle in two dimensions, laterally (as in FIG. 4) and axially, allowing the needle tip to be engaged in the mouth of the needle guard after the needle has already passed the grasping thumb and fingers. The diagonal tab can be varied at will without essentially changing its character by making the diagonally-projecting tab L-shaped or J-shaped.

A further preferred feature is also shown in FIG. 6, namely that the opening (3) at the end of the needle guard is flared in the shape of a funnel to facilitate positive engagement of the needle tip. The cross-sectional area of the improved opening should be at least about twice the cross-sectional area of the main body of the needle guard. The funnel depth can vary, at will, but should provide sufficient clearance to avoid contact with the needle hub and syringe.

What I claim is:

1. In a needle guard for a hypodermic syringe comprising a substantially cylindrical hollow body, having a first end that is open and a second end that is closed, adapted to receive the needle of a hypodermic syringe by means of insertion into the first end of the guard, the improvement wherein said guard has attached to an external surface thereof and projecting therefrom, closer to the first end than the second end thereof, a tab of a size and shape to be readily grasped between the thumb and forefinger of a user for insertion of the needle into the first end of the needle guard without accidental stabbing of the user's hand, wherein the axis of the needle guard lies in the plane of the tab, and wherein the needle guard has further attached to an external surface thereof a substantially planar sheet-like shield, attached immediately next to the tab between said tab and said first end of the body of the needle guard, the plane of said shield being substantially bisected by th projecting edge of said tab and intersecting the body of the needle guard perpendicularly to the length of said body.

2. The improved needle guard of claim 1, wherein said needle guard body, tab and shield are all molded of the same thermoplastic material at the same time in the same mold.

* * * * *